United States Patent [19]

Parker et al.

[11] Patent Number: 4,977,185
[45] Date of Patent: Dec. 11, 1990

[54] ANTIRETROVIRAL ARYLOXY SUBSTITUTED FURAN KETONES

[75] Inventors: Roger A. Parker; Sai P. Sunkara, both of Cincinnati, Ohio

[73] Assignee: Merrell Dow Pharmaceuticals, Cincinnati, Ohio

[21] Appl. No.: 438,541

[22] Filed: Nov. 27, 1989

Related U.S. Application Data

[63] Continuation-in-part of Ser. No. 287,817, Dec. 21, 1988, abandoned.

[51] Int. Cl.$^5$ .............................................. A61K 31/34
[52] U.S. Cl. .................................. 514/473; 514/461; 549/479; 549/488
[58] Field of Search ................. 549/488, 479; 514/461, 514/473

[56] References Cited

U.S. PATENT DOCUMENTS

| | | | |
|---|---|---|---|
| 4,000,164 | 12/1976 | Parker | 549/479 |
| 4,171,371 | 10/1979 | Diana | 514/461 |
| 4,382,814 | 5/1983 | Steffens | 549/479 |
| 4,602,099 | 7/1986 | Parker | 549/479 |
| 4,738,984 | 4/1988 | Parker | 514/473 |

FOREIGN PATENT DOCUMENTS

2518999 7/1983 France .
1539636 12/1977 United Kingdom .

OTHER PUBLICATIONS

G. D. Mayer, et al., RMI 15,731, A New Antirhinovirus Compound, Intersci. Conf. Antimicrob. Agents Chemother., Atlanta, 1-4 Oct., 1978, (18th Conf.)(Abst 220).
R. J. Ash, et al., RMI 15,731, An Inhibitor of Rhinovirus Replication. Intersci. Conf. Antimicrob. Agents Chemother., Atlanta, 1-4 Oct., 1978, (18th Conf.)(Abst 221).
Ash, Ronald J., et al., RMI 15,731 (1-[5-tetradecyloxy-2-furanyl]-ethanone), A New Antirhinovirus Compound. Antimicrob. Agents Chemother., 16(3), 301-5 (1979).
Anon. RMI-15731, Drugs of the Future 5, 306-7 (1980).
F. E. Hanh, Coming Drugs Against the Common Cold? Naturwissenschaften 66, 417-8 (1979).
Chemical Abstracts 102(23):197597d, Ninomiya, Y., et al., Comparative Studies on the Modes of Action of the Antirhinovirus Agents Ro 09-0410, Ro 09-0179, RMI--15,731, 4',6-dichloroflavan, and Enviroxime. Antimicrob. Agents Chemother., 27(4), 595-9 (1985).
Chemical Abstracts 106((1):197b, Ninomiya, Y., et al., Mechanism of Drug Resistance to Anti-Rhinovirus Agents Recent Adv. Chemother., Proc. Int. Congr. Chemother., 14th, Issue Antimicrobial Sect. 1,379-80, Edited by: Ishigami, Joji, Univ. Tokyo Press: Tokyo, Japan. (1985).
Chemical Abstracts 106(13):95652h, Ishitsuka, H., et al., Molecular Basis of Drug Resistance to New Antirhinovirus Agents, J. Antimicrob. Chemother., 18, (Suppl. B), 11-18 (1986).
Parker, Roger A., et al., 5-(Tetradecyloxy)-2-Furan-Carboxylic Acid and Related Hypolipidemic Fatty Acidlike Alkyloxyarylcarboxylic Acids., J. Med. Chem., 20 (6), 781-91 (1977).

Primary Examiner—Donald G. Daus
Attorney, Agent, or Firm—Edlyn S. Simmons

[57] ABSTRACT

Novel furan ketone derivatives having antiretrovirus activity and effective in a method of treatment of a retrovirus infection, have the formula

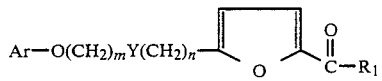

wherein Y represents a bond, oxygen or divalent sulfur; Ar represents phenyl or naphthylenyl; n is 0 or 1; m is an integer of from 4 to 10; and $R_1$ represents $C_{1-6}$ alkyl.

32 Claims, No Drawings

ANTIRETROVIRAL ARYLOXY SUBSTITUTED FURAN KETONES

This is a continuation in part of U.S. Ser. No. 287,817, filed Dec. 21,1988, now abandoned.

FIELD OF INVENTION

The present invention relates to the use of certain aryloxy substituted furan alkyl ketones in the treatment of retroviral infections including HIV infections.

BACKGROUND OF THE INVENTION

A great deal of research is currently underway to develop treatments and cures for viral infections in humans and in animals. Notably the incidence of acquired immune deficiency syndrome (AIDS) and AIDS related complex (ARC) in humans is increasing at an alarming rate. The five year survival rate for those with AIDS is dispiriting and AIDS patients, whose immune systems have been seriously impaired by the infection, suffer from numerous opportunistic infections including Kaposi's sarcoma and *Pneumocystis carninii* pneumonia. No cure is known and current treatments are largely without adequate proof of efficacy and have numerous untoward side effects. Fear of the disease has resulted in social ostracism of and discrimination against those having or suspected of having the disease.

Retroviruses are a class of ribonucleic acid (RNA) viruses that replicate by using reverse transcriptase to form a strand of complementary DNA (cDNA) from which a double stranded, proviral DNA is produced. This proviral DNA is then randomly incorporated into the chromosomal DNA of the host cell. Further transcription and translation of the integrated viral genome DNA results in viral replication through the synthesis of virus specific RNA and proteins.

Many of the known retroviruses are oncogenic or tumor causing. Indeed the first two human retroviruses discovered, denoted human T-cell leukemia virus I and II or HTLV-I and II, were found to cause rare leukemias in humans after infection of T-lymphocytes. The third such human virus to be discovered, HTLV-III, now referred to as HIV, was found to cause cell death after infection of T-lymphocytes and has been identified as the causative agent of acquired immune deficiency syndrome (AIDS) and AIDS related complex (ARC).

Among the substances previously shown to have activity against HIV and other retroviruses are such diverse compounds as azidothymidine, castanospermine, and heparin.

The applicants have now discovered that certain substituted furan ketones, more specifically furan ketones substituted at the 5-position of the furan ring by phenoxyalkyl and naphthylenyloxyalkyl moieties bonded to the furan ring either directly, through an ether or thioether bridge, or through an oxymethyl or thiomethyl bridge, are useful in the treatment of various retroviral infections including in the treatment of AIDS and ARC resulting from infection by HIV or other retroviruses.

SUMMARY OF THE INVENTION

The anti-retrovirus compounds of this invention have the general Formula I

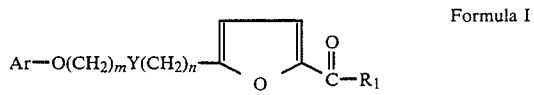

In the above general Formula I, Y is a bond, oxygen or divalent sulfur, n is 0 or 1, Ar is phenyl or naphthylenyl, m is from 4 to 10, and $R_1$ is $C_{1-6}$ alkyl.

DETAILED DESCRIPTION OF THE INVENTION

In the above general Formula I, when Ar is naphthylenyl, the compounds have the general Formula II

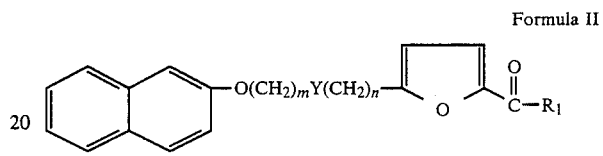

wherein the naphthylenyl substituent may be attached to the oxygen atom through the 1- or 2-position.

In the above general Formula I, when Ar is phenyl, the compounds have the general formula III.

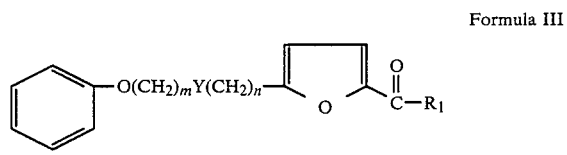

The linear, saturated carbon chain linking the ether with Y may range in length from 4 to 8 carbon atoms. Compounds having a chain length of 6 to 8 methylene units are preferred, with a chain length of 6 methylene units being most preferred.

Illustrative examples of straight or branched lower alkyl groups of from 1 to 6 carbon atoms which $R_1$ may represent are methyl, ethyl, n-propyl, isopropyl, n-butyl, tert-butyl, neopentyl, and n-hexyl.

The naphthylenyloxy substituted compounds of general Formula II represent a preferred embodiment of this invention. Of the compounds of general Formula I, those wherein Y is oxygen are more preferred. Also, the compounds of general Formula I wherein $R_1$ is a straight chain alkyl are preferred over the branched chain alkyl derivatives. Compounds wherein $R_1$ is methyl are particularly preferred. Also, the compounds of general Formula I wherein m is from 6–8 are preferred, 6 being most preferred. Another preferred embodiment of this invention is a pharmaceutical composition for the treatment of retrovirus infection comprising a compound of Formula I and a pharmaceutically acceptable carrier.

Another preferred embodiment of this invention is the use of compounds of general Formula I as antiretrovirus agents. The use of compounds of general Formula I wherein $R_1$ is a straight chain alkyl group are preferred, with $R_1$ as methyl being more preferred. Another preferred embodiment is the use of compounds of general Formula I as antiretrovirus agents wherein Ar is naphthylenyl. The use of compounds of general Formula I wherein Y is oxygen or sulfur is another preferred embodiment, with Y as oxygen being more preferred.

Illustrative examples of compounds of general Formula I are the following:

methyl 5-[6-(2-naphthylenyloxy)hexyloxy]-2-furyl ketone,
ethyl 5-[8-(1-naphthylenyloxy)octyloxy]-2-furyl ketone,
n-propyl 5-[7-(1-naphthylenyloxy)heptylthio]-2-furyl ketone,
methyl 5-[(C6-(2-anphthylenyloxy)hexyl)oxymethyl]-2furyl ketone,
isopropyl 5-[(4-(2-naphthylenyloxy)butyl)thiomethyl]-2-furyl ketone,
methyl [5-(2-naphthylenyloxy)pentyl]-2-furyl ketone,
methyl 5-(6-phenoxyhexyloxy)-2-furyl ketone,
ethyl 5-(10-phenoxydecyloxy)-2-furyl ketone,
n-propyl 5-(8-phenoxyoctylthio)-2-furyl ketone,
methyl 5-(9-phenoxynonlyoxymethyl)-2-furyl ketone,
isopropyl 5-(7-phenoxyheptylthiomethyl)-2-furyl ketone,
methyl 5-(6-phenoxyhexyl)-2-furyl ketone, The ability of the furan ketone derivatives of this invention to act as anti-retroviral agents can be demonstrated by their ability to inhibit the growth and replication of murine leukemia virus, an oncogenic retrovirus, as determined by an in vitro XC plaque assay. This assay was performed according to the method of Rowe et al. (*Virology*, 1970, 42, 1136–39) as previously described by L. Hus, et al. (*J. Virological Methods*, 1980, 1, 167–77) and T. L. Bowlin and M. R. Proffitt (*J. Interferon Res.*, 1983, 3(1), 19–31). Mouse SC-1 cells (fibroblast) ($10^5$) were seeded into each well of 6-well cluster plates (Costar #3506) in 4 ml Minimum Essential Medium (MEM) with 10% Fetal Calf Serum (FCS). Following an 18 hour incubation period (37° C.), Moloney murine leukemia virus (MoLV) was applied at a predetermined titer to give optimal (i.e. countable) numbers of virus plaques. Methyl 5-[6-(2-naphthylenyloxy)hexyloxy]-2-furyl ketone was added 2 hours prior to addition of the virus at various concentrations. Three days later the culture medium was removed, the SC-1 cell monolayers were exposed to UV irradiation (1800 ergs), and rat XC cells ($10^6$) were seeded into each well in 4 ml MEM. Following an additional 3 day incubation (37° C.), these cells were fixed with ethyl alcohol (95%) and stained with 0.3% crystal violet. Plaques were then counted under low magnification. The $IC_{50}$, i,e, the concentration giving a 50% inhibition of virus plaque growth, was below 1 μg/ml, indicating the exceptional antiviral activity of the tested compound of this invention.

The furan ketone derivatives of this invention can be used to treat a number of diseases and conditions known to be caused by retroviruses including those diseases and conditions caused by murine leukemia virus, feline leukemia virus, avian sarcoma virus, human immunodeficiency virus (HIV), HTLV-I, and HTLV-II. Those experienced in this field are readily aware of the circumstances requiring anti-retroviral therapy. Applicants consider the use of the furan ketone derivatives of this invention to treat HIV infections in humans to be of most importance. The term "patient" used herein is taken to mean mammals such as primates, including humans, sheep, horses, cattle, pigs, dogs, cats, rats and mice, and birds.

The amount of the furan ketone derivative of formula I to be administered can vary widely according to the particular dosage unit employed, the period of treatment, the age and sex of the patient treated, the nature and extent of the disorder treated, and the particular furan ketone derivative selected. Moreover the furan ketone derivative can be used in conjunction with other agents known to be useful in the treatment of retroviral diseases and agents known to be useful to treat the symptoms of and complications associated with diseases and conditions caused by retroviruses. The anti-retrovirally effective amount of a furan ketone derivative of formula I to be administered will generally range from about 15 mg/kg to 500 mg/kg. A unit dosage may contain from 25 to 500 mg of the furan ketone derivative, and can be taken one or more times per day. The furan ketone derivative can be administered with a pharmaceutical carrier using conventional dosage unit forms either orally or parenterally.

The preferred route of administration is oral administration. For oral administration the furan ketone derivative can be formulated into solid or liquid preparations such as capsules, pills, tablets, troches, lozenges, melts, powders, solutions, suspensions or emulsions. The solid unit dosage forms can be capsules, which can be of the ordinary hard- or soft-shelled gelatin type containing, for example, surfactants, lubricants, and inert fillers such as lactose, sucrose, calcium phosphate and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration, such as potato starch, alginic acid, corn starch and guar gum, lubricants intended to improve the flow of tablet granulations and to prevent the adhesion of tablet material to the surfaces of the tablet dies and punches, for example, talc, stearic acid, or magnesium, calcium or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The furan ketone derivatives of this invention may also be administered parenterally, that is, subcutaneously, intravenously, intramuscularly or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol or hexadecyl alcohol, glycols such as propylene glycol or polyethylene glycol, glycerol ketals such as 2,2-dimethyl-1,3-dioxolane-4-methanol, ethers such as[poly(ethylene glycol) 400, an oil, a fatty acid, a fatty acid ester or glyceride, or an acetylated fatty acid glyceride, with or without the addition of a pharmaceutically acceptable surfactant such as a soap or a detergent, a suspending agent such as pectin, carbomers, methylcellulose, hydroxypropylmethylcellulose or carboxymethylcellulose, or an emulsifying agent, and other pharmaceutical adjuvants. Illustrative of oils which can be used in the parenteral formulations of this invention are those of petroleum, animal, vegetable, and synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl β-aminopropionates and 2-alkylimidaxoline quarternary ammonium salts, as well as mixtures. The parenteral compositions of this invention will typically contain from about 0.5 to about 25% by weight of the furan ketone derivative of formula 1 in solution. Preservatives and buffers may also be used advantageously. In order to minimize or eliminate irritation at the site of injection, such compositions may contain a non-ionic surfactant having a hydrophilelipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The ketone compounds of general Formula I may be prepared by treating one equivalent of the corresponding carboxylic acid derivatives with two equivalents of alkyllithium, wherein the alkyl group corresponds to the desired $R_1$ substituent, as generally described by Fieser and Fieser, Reagents for Organic Synthesis, J. Wiley and Sons, Inc., New York, p. 688 (1967). This reaction is suitably carried outin solvents such as ether, tetrahydrofluran, p-dioxane, dimethoxyethane or diethyleneglycol dimethylether at temperatures of from $-10°$ C. to the reflux temperature of the solvent for from ½ hour to 10 hours.

The ketone compounds of general Formula I may also be prepared by the reaction of alkyl magnesium bromide wherein the alkyl group corresponds to the desired $R_1$ substituent and the imidazolide derivative of an appropriately 5-ArO(CH$_2$)$_m$Y(CH$_2$)$_n$ substituted 2-furancarboxylic acid derivative wherein Ar, Y, m and n have the meanings defined in general Formula I. This reaction is carried out in a solvent such as ether, tetrahydrofuran, dioxane, dimethoxyethane, or acetonitrile. The reaction mixture is initially cooled to $-10°$ C., after which the temperature is elevated to from about 25° C. to the reflux temperature of the solvent, and the reaction time varies from about ½ hour to 10 hours. The imidazolide derivative is obtained by treating an appropriate 5-ArO(CH$_2$)$_m$Y(CH$_2$)$_n$ substituted 2-furancarboxylic acid derivative with N,N'-carbonyldiimidazole or by treatment of the 5-Ar(CH$_2$)Y(CH$_2$)$_n$ substituted 2-furancarboxylic acid chloride, obtained by treating the substitutted carboxylic acid with thionyl chloride, with two equivalents of imidazole, as generally described by H. A. Staab, Angew. Chem. Internat. Edit. 1, 351 (1962).

The compounds of general Formula I may also be prepared by a Friedel-Crafts acylation of an appropriately ArO(CH$_2$)mY(CH$_2$)$_n$ substituted furan, wherein Ar, Y, m and n have the meanings defined in general Formula I, with an acyl halide of the formula

wherein halo is halogen, preferably chlorine or bromine and $R_1$ has the meaning defined above. This reaction is carried out in the presence of an acid catalyst, for example, borontrifluoride-etherate, stannic chloride, zinc chloride, hydriodic acid or orthophosphoric acid, and optionally in the presence of a solvent, for example, methylene chloride, nitromethane or benzene. Suitable temperatures for this reaction may vary from $-20°$ C. to the reflux temperature of the solvent and the reaction time varies from about ½ hour to 10 hours.

The ArO(CH$_2$)mO- and ArO(CH$_2$)mS- substituted furancarboxylic acid derivative used herein can be prepared by aromatic nucleophilic substitution as generally described in J. March, Advanced Organic Chemistry: Reactions, Mechanisms and Structure, McGraw-Hill, p. 500 (1968), as outlined below.

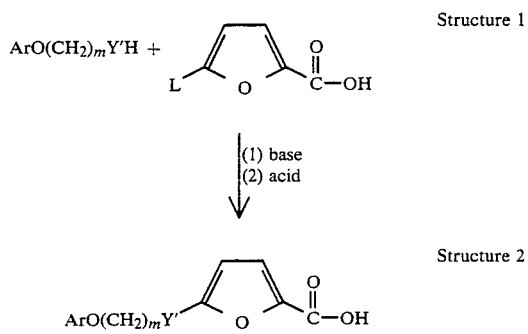

In the above general reaction, Ar and m have the meanings defined in general Formula I, Y' represents oxygen or divalent sulfur, and L represents a leaving group, such as nitro, fluoro, chloro, bromo or iodo, the preferred leaving group being chloro.

The above reaction may be carried out with or without a solvent. Suitable solvents for the reaction include benzene, xylene, toluene, chlorinated hydrocarbon solvents such as chlorobenzene, ethers such as bis(2-methoxyethyl) ether, 1,2-dimethoxyethane or anisole, hexamethylphosphoric triamide (HMPA), dimethylformamide, dimethylacetamide, 1-methyl-2-pyrrolidone, or pyridine. Preferred solvents are xylene, toluene and dimethylacetamide. Copper metal or a salt such as cuprous chloride may optionally be added to the reaction. Suitable bases for the reaction induce sodium or potassium metal, sodium hydride, potassium aside, potassium tert-butoxide or other strong bases such as potassium carbonate, potassium hydroxide, sodium hydroxide and sodium carbonate. The temperature of the reaction varies from about 25° C. to the reflux temperature of the solvent, and the reaction time varies from about 1 hour to about 7 days. Following completion of the reaction, the carboxylate salt derivative is treated with a mineral or organic acid to give compounds of structure 2.

The furoic acid derivatives represented by compounds of structure 1 may be prepared by several methods, as described in The Furans, by A. P. Dunlop and F.

N. Peters, Reinhold Publishing Corp., pp. 80–169 (1953).

The 5-ArO(CH$_2$)$_m$Y(CH$_2$)$_n$ substituted furan carboxylic acid derivatives employed herein wherein Y is a bond and n is 0 can be prepared by treating a compound of the structure

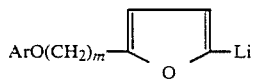
Structure 3 wherein Ar and m have the meanings defined in general Formula I with dry ice followed by the addition of water by procedures known in the art. The compounds of structure 3 are obtained by metalation of the appropriately substituted furan with butyllithium.

ArO(CH$_2$)$_m$Y- substituted furan derivatives wherein Y is a bond can be obtained by the reaction of 2-lithiofuran, prepared by treating furan with butyllithium, with an ArO(CH$_2$)$_m$ halide wherein Ar and m have the meanings defined in general Formula I by procedures generally known in the art. The ArO(CH$_2$)$_m$ halides used herein are commercially available or may be prepared by well-known procedures.

Likewise, the ArO(CH$_2$)$_m$—Y'CH$_2$- substituted furan carboxylic acid derivatives can be prepared by metalation followed by addition of carbon dioxide (carboxylation) as illustrated below.

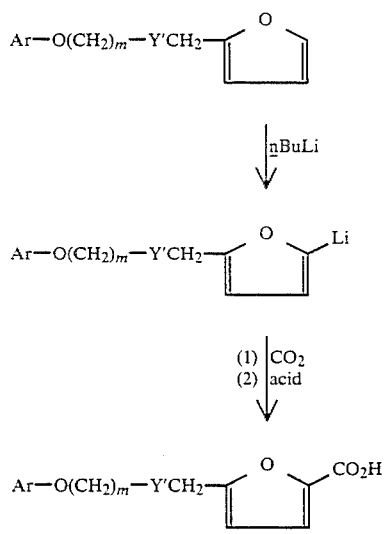

The ArO(CH$_2$)$_m$OCH$_2$- and ArO(CH$_2$)mSCH$_2$- substituted furans can be obtained by reaction of furfuryl alcohol or furfuryl mercaptan by Williamson ether synthesis (J. March, *Advanced Organic Chemistry—Reactions, Mechanisms and Structure*, McGraw-Hill Book Company, New York, 1968, p. 316). The reaction is illustrated in the following reaction scheme:

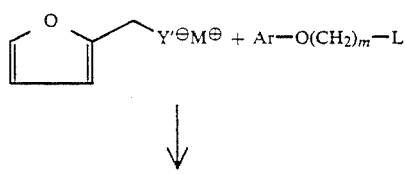

In the above reaction sequence, L represents a halogen atom, such as chlorine, bromine or iodine, or a sulfonate ester, such as methanesulfonate or p-toluenesulfonate; M$^+$ represents a metal salt such as lithium, sodium, potassium, silver or mercury, and Ar, m and Y' have the meanings described above.

A furfuryl alkoxide salt, conveniently formed in situ by addition of a base such as sodium methoxide, potassium carbonate, sodium hydride or potassium hydroxide to the corresponding alcohol or mercaptan, is reacted with the desired aryl alkyl ether bearing a leaving group on the terminal carbon atom. The leaving group is displaced, resulting in the formation of a carbon-oxygen or carbon-sulfur ether bond.

The L-substituted aryl alkyl ethers used in the sequence are generally available commercially or by well-known, conventional synthetic methods.

The ArO(CH$_2$)$_m$Y'CH$_2$- substituted furan carboxylic acid derivative used herein may also be prepared from an ester of 5-methylfuran carboxylic acid by a Williamson ether synthesis as shown in the reaction scheme below:

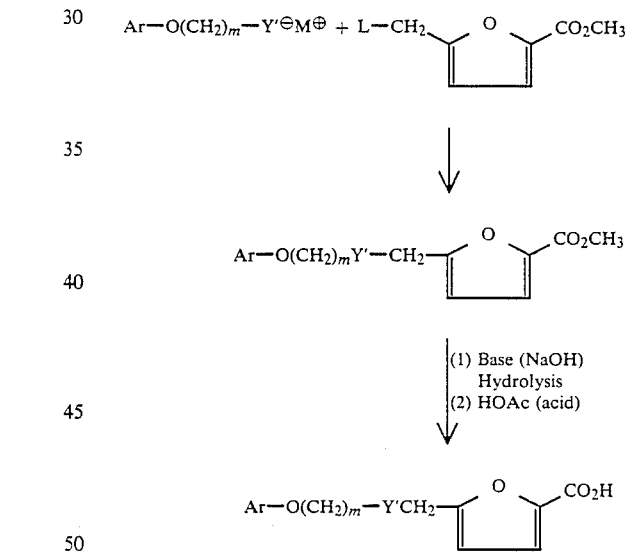

An alkoxide salt, conveniently formed in situ by addition of a base such as sodium methoxide, potassium carbonate, sodium hydride or potassium hydroxide to the aryloxyalkyl alcohol or mercaptan having the desired ArO(CH$_2$)$_m$ skeleton, is reacted with a 5-methylfuroic acid ester bearing a leaving group on the methyl carbon atom. The leaving group is displaced, resulting in the formation of a carbon-oxygen or carbon-sulfur ether bond, and the resulting 5-ArO(CH$_2$)$_m$Y'(CH$_2$)$_n$-substituted 2-furoic acid ester is hydrolyzed to the desired acid by methods well known in the art.

The substituted furoic acid esters used in the sequence are generally available commercially or by well-known, conventional synthetic methods. The aryloxyalkyl alcohols and mercaptans may be prepared by well-known, conventional synthetic methods, for example by the Williamson reaction between a phenoxide or naphthoxide salt and an alkanol substituted by a leaving group on the terminal carbon atom, as illustrated in the following reaction scheme:

$$ArO^\ominus M^\oplus + L-(CH_2)_m-Y'H \rightarrow ArO(CH_2)_m Y'H$$

In the above reaction sequence, L represents a halogen atom, such as chlorine, bromine or iodine, or a sulfonate ester such as methanesulfonate or p-toluenesulfonate; M+ represents a metal ion such as lithium, sodium, potassium, silver or mercury; and Ar and n are as defined for Formula I. The starting naphthols and phenol which are the precursors of the naphthoxide and phenoxide salts are commercially available. The ω-substituted linear alcohols and mercaptans, III, used in the sequence are also generally available commercially or by well-known, conventional synthetic methods. For example, the α,ω-diol may be converted to the ω-haloalcohol using triphenylphosphine and carbon tetrahalide.

The Williamson reaction may be carried out with or without solvents. Suitable solvents for the reaction incude lower alcohols, such as ethanol and isopropanol, ketones such as acetone and butanone, or amides such as dimethylformamide and dimethylacetamide. Other suitable solvents include dimethylsulfoxide, acetonitrile, dimethoxyethane, tetrahydrofuran and toluene.

The temperature of the reaction may vary from about 0° C. to the reflux temperature of the solvent, and the reaction time may vary from about 0.5 hour to 80 hours.

The reaction is conveniently worked up by extraction of the product into an organic solvent such as ether, dichloromethane, chloroform, toluene or the like, washing with brine, drying over sodium or magnesium sulfate, and evaporation of the solvent. Purification is generally effected by distillation or crystallization from a suitable solvent.

EXAMPLE 1

Methyl 5-[6-(2-naphthalenyloxy)hexyloxy]-2-furyl]ketone

A mixture of 50.0 g (0.348 mole) of 2-naphthol, 18.8 g (0.348 mole) of sodium methoxide, 2.0 g of sodium iodide and 800 ml of dimethylacetamide was stirred at room temperature for 1 hour, 47.5 g (0.348 mole) of 6-chlorohexanol was added. The mixture was heated to reflux with stirring for two hours, allowed to cool and poured into 3 liters of water and extracted with diethylether. The ether layer was evaporated to dryness to give a solid residue which was recrystallized from methanol to give 13.3 g of 6-(2-naphthalenyloxy)hexanol, mp=64°-65° C.

A mixture of 12.2 g (0.05 mole) of 6-(2-naphthalenyloxy)hexanol, 4.8 g (0.10 mole ) of 50% sodium hydride in oil and 200 ml of toluene was stirred at room temperature for 1 hour, 50 ml of hexamethylphosphoric triamide (HMPA) was added and the mixture refluxed for 2 and ½ hours. 7.3 g (0.05 mole) of 5-chloro-2-furancarboxylic was acid was added and the mixture was refluxed for sixteen hours, then allowed to cool and was diluted with water. The mixture was acidifed by addition of glacial acetic acid and extracted with diethylether. The ether layer was washed with water and filtered. Evaporation of the mixture to about 100 ml volume gave 8.6 g (43%) tan solid 5-[6-(2-napthalenlyoxy) hexyloxy)]-2-furancaboylic acid, mp 127°-129° C.

A mixture of 5.0 g (0.0125 mole) of 5-[6-(2-napthalenlyoxy)hexyloxy]-2-furancarboxyl acid and 100 ml of anhydrous ether was stirred at room temperature. Methyllithium (18 ml of a 1.55 molar solution, 0.028 mole) was added dropwise with stirring over 20 minutes. The mixture stood for 30 minutes, then 30 ml of tetrahydrofuran was added and the mixture refluxed. 10 ml of hexamethylphosphoric triamide (HMPA) was added and the reaction stirred at room temperature for 2 hours. Saturated ammonium chloride in water (200 ml) was added and the layers were separated. The ether layer was washed with water and filtered through alumina and was evaporated to dryness under reduced pressure to give 4.6 g of a light brown solid. Recrystallization from acetonitrile and then from ethanol gave 1.1 g of a light tan solid, methyl 5-[6-2-napthalenyloxy)hexyloxy]-2-furyl ketone, mp=94°-100° C.

EXAMPLE 2

Methyl 5-(6-phenoxyhexyloxy-)2)-furyl ketone

When phenol was substituted for 2-naphthol in the procedure of Example 1, methyl 5-(6-phenoxyhexyloxy)2-furyl ketone was obtained, mp=80°=82° C.

EXAMPLE 3

Methyl 5-(10-phenoxydecyloxy)-2-furyl ketone

When phenol was substituted for 2-naphthol and 1-chlorodecanol was substituted for 6-chlorohexanol in the procedure of Example 1, methyl 5-(10-phenoxydecyloxy)-2-furyl ketone was obtained, mp=74°-77° C.

EXAMPLE 4

Solution

| | |
|---|---|
| Methyl 5-[6-(2-naphthalenyloxy)hexyloxy]-2-furyl] ketone | 0.85 g |
| Alcohol | 78.9 ml |
| Isopropyl Myristate | 5.0 g |
| Polyethylene Glycol 400 (Av. M.W. 400) | 10.0 g |
| Purified Water sufficient to make | 100 ml |

Combine the alcohol, isopropyl myristate and polyethylene glycol 400 and dissolve the drug substance therein. Add sufficient purified water to give 100 ml.

EXAMPLE 5

Tablet For 15,000

| | |
|---|---|
| Methyl 5-[6-(2-naphthalenyloxy)hexyloxy]-2-furyl] ketone | 75 g |
| Lactose | 1.216 kg |
| Corn Starch | 0.3 kg |

Mix the active ingredient, the lactose and corn starch uniformly. Granulate with 10% starch paste. Dry to a moisture content of about 2.5%. Screen through a No.12 mesh screen. Add and mix the following:

| | |
|---|---|
| Magnesium | 0.015 kg |
| Corn Starch sufficient to make | 1.725 kg |

Compress on a suitable tablet mechine to a weight of 0.115 g/tablet.

EXAMPLE 6

Soft Gelatin Capsule

| | |
|---|---|
| Methyl 5-(6-phenoxyhexyloxy)-2-furyl ketone | 0.25 kg |
| Polysorbate 80 (Polyoxyethylene (20) sorbitan mono-oleate) | 0.25 kg |
| Corn Oil sufficient to make | 25.0 kg |

Mix and fill into 50,000 soft gelatin capsules.

What is claimed is:

1. A compound of the formula

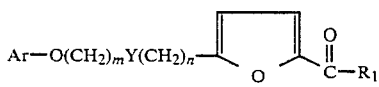

wherein Y represents a bond, oxygen or divalent sulfur; Ar represents phenyl or naphthylenyl; n is 0 or 1; m is an integer of from 4 to 10; and $R_1$ represents $C_{1-6}$ alkyl.

2. A compound according to claim 1 wherein Ar is 1- or 2-naphthylenyl.

3. A compound according to claim 1 wherein Y is oxygen.

4. A compound according to claim 1 wherein m is an integer of from 5 to 7.

5. A compound according to claim 1 wherein m is 6.

6. The compound according to claim 1 wherein the compound is methyl 5-[6-(2-naphthylenyloxy)hexyloxy]-2-furyl ketone.

7. The compound according to claim 1 wherein the compound is methyl 5-(6-phenoxyhexyloxy)-2-furyl ketone.

8. The compound according to claim 1 wherein the compound is methyl 5-(10-phenoxydecyloxy)-2-furyl ketone.

9. A method of treating a retroviral infection in a patient in need thereof which comprises administering to the patient an anti-retrovirally effective amount of a compound of the formula:

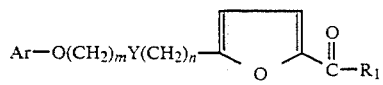

wherein Y represents a bond, oxygen or divalent sulfur; Ar represents phenyl or naphthylenyl; n is 0 or 1; m is an integer of from 4 to 10; and $R_1$ represents $C_{1-6}$ alkyl.

10. A method according to claim 9 wherein Ar is 1- or 2-naphthlenyl.

11. A method according to claim 9 wherein Y is oxygen.

12. A method according to claim 9 wherein m is an integer of from 5 to 7.

13. A method according to claim 9 wherein m is 6.

14. The method according to claim 9 wherein the compound is methyl 5-[6-(2-naphthylenyloxy)hexyloxy]-2-furyl ketone.

15. The method according to claim 9 wherein the compound is methyl 5-(6-phenoxyhexyloxy)-2-furyl ketone.

16. The method according to claim 9 wherein the compound is methyl 5-10-phenoxydecyloxy)-2-furyl ketone.

17. A pharmaceutical composition which comprises a compound of the formula

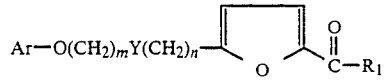

wherein Y represents a bond, oxygen or divalent sulfur; Ar represents phenyl or naphthylenyl; n is 0 or 1; m is an integer of from 4 to 10; and $R_1$ represents $C_{1-6}$ alkyl; and a pharmaceutically acceptable carrier.

18. A pharmaceutical composition according to claim 17 wherein Ar is 1- or 2-naphthylenyl.

19. A pharmaceutical composition according to claim 17 wherein Y is oxygen.

20. A pharmaceutical composition according to claim 17 wherein m is an integer of from 5 to 7.

21. A pharmaceutical composition according to claim 17 wherein m is 6.

22. A pharmaceutical composition according to claim 17 wherein the compound is methyl 5- [6-(2-naphthylenyloxy) hexyloxy]-2-furyl ketone.

23. A pharmaceutical composition according to claim 17 wherein the compound is methyl 5-(6-phenoxyhexyloxy)-2-furyl ketone.

24. A pharmaceutical composition according to claim 17 wherein the compound is methyl 5-(10-phenoxydecyloxy)-2-furyl ketone.

25. A composition which comrises a compound of the formula

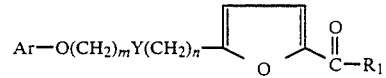

wherein Y represents a bond, oxygen or divalent sulfur; Ar represents phenyl or naphthylenyl; n is 0 or 1; m is an integer of from 4 to 10; and $R_1$ represents $C_{1-6}$ alkyl; and an inert carrier.

26. A composition according to claim 25 wherein Ar is 1- or 2-naphthylenyl.

27. A composition according to claim 25 wherein Y is oxygen.

28. A composition according to claim 25 wherein m is an integer of from 5 to 7.

29. A composition according to claim 25 wherein m is 6.

30. A composition according to claim 25 wherein the compound is methyl 5-[6-(2-naphthylenyloxy)hexyloxy]-2-furyl ketone.

31. A composition according to claim 25 wherein the compound is methyl 5-(6-phenoxyhexyloxy)-2-furyl ketone.

32. A composition according to claim 25 wherein the compound is methyl 5-(10-phenoxydecyloxy)-2-furyl ketone.

* * * * *